United States Patent [19]

Goldrath

[11] Patent Number: 5,451,208
[45] Date of Patent: * Sep. 19, 1995

[54] ENDOMETRIUM COAGULATING APPARATUS AND SURGICAL METHOD FOR THERMAL DESTRUCTION OF THE ENDOMETRIUM

[76] Inventor: Milton H. Goldrath, 31074 Oakleaf, Franklin, Mich. 48025

[*] Notice: The portion of the term of this patent subsequent to Sep. 7, 2010 has been disclaimed.

[21] Appl. No.: 115,994

[22] Filed: Sep. 2, 1993

Related U.S. Application Data

[63] Continuation of Ser. No. 695,636, May 3, 1991, Pat. No. 5,242,390.

[51] Int. Cl.⁶ .................................... A61M 31/00
[52] U.S. Cl. ............................. 604/55; 604/54; 604/48; 604/49; 604/113; 604/117; 606/27; 606/135; 606/159; 607/104; 607/96
[58] Field of Search ...................... 604/27–28, 604/30, 43, 48–49, 54–55, 268, 117, 113, 279, 283; 606/27, 172; 128/4, 6–7, 24.1; 607/96, 104, 105

[56] References Cited

U.S. PATENT DOCUMENTS

| | | |
|---|---|---|
| 1,652,954 | 12/1927 | Pierce ............................ 607/105 |
| 2,043,083 | 6/1936 | Wappler . |
| 2,074,634 | 3/1937 | Ackermann . |
| 2,077,453 | 4/1937 | Albright . |
| 2,078,786 | 4/1937 | Wood . |
| 2,190,384 | 2/1940 | Newman . |
| 2,192,768 | 3/1940 | Cross . |
| 2,212,706 | 8/1940 | Cohn et al. .................. 604/55 |
| 2,466,042 | 4/1949 | Reich et al. . |
| 2,734,508 | 2/1956 | Kozinski . |
| 2,777,445 | 1/1957 | Hart . |
| 3,369,549 | 2/1968 | Armao . |
| 3,401,689 | 9/1968 | Greenwood ...................... 604/55 |
| 3,417,746 | 12/1968 | Moore et al. . |
| 3,509,877 | 5/1970 | Weiss ................................. 604/55 |
| 3,850,162 | 11/1974 | Iglesias . |
| 3,924,628 | 12/1975 | Droegemueller et al. . |
| 4,245,623 | 1/1981 | Erb . |
| 4,601,698 | 7/1986 | Moulding, Jr. ................. 604/55 |
| 4,606,336 | 8/1986 | Zeluff ............................ 604/55 |
| 4,637,814 | 1/1987 | Leiboff . |
| 4,775,362 | 10/1988 | Kronner ......................... 604/55 |
| 4,779,612 | 10/1988 | Kishi . |
| 4,795,424 | 1/1989 | Burner . |
| 4,836,189 | 6/1989 | Allred, III et al. . |
| 4,949,718 | 8/1990 | Neuwirth et al. . |
| 5,084,044 | 1/1992 | Quint . |
| 5,211,631 | 5/1993 | Sheaff ........................... 604/113 |
| 5,242,390 | 9/1993 | Goldrath . |
| 5,257,977 | 11/1993 | Eshel ............................ 604/113 |

FOREIGN PATENT DOCUMENTS

WO88008 9/1988 WIPO .

Primary Examiner—Randall L. Green
Assistant Examiner—P. Zuttarelli
Attorney, Agent, or Firm—Gifford, Krass, Groh, Sprinkle, Patmore, Anderson & Citkowski

[57] ABSTRACT

Apparatus and surgical procedures are provided for completely coagulating endometrial tissue of the uterus by means of heated liquid in the distended uterus under direct view of a thermally insulated hysteroscope or under indirect view fluoroscopically using a thermally insulated hysterographic cannula and a radiopaque heated liquid.

9 Claims, 4 Drawing Sheets

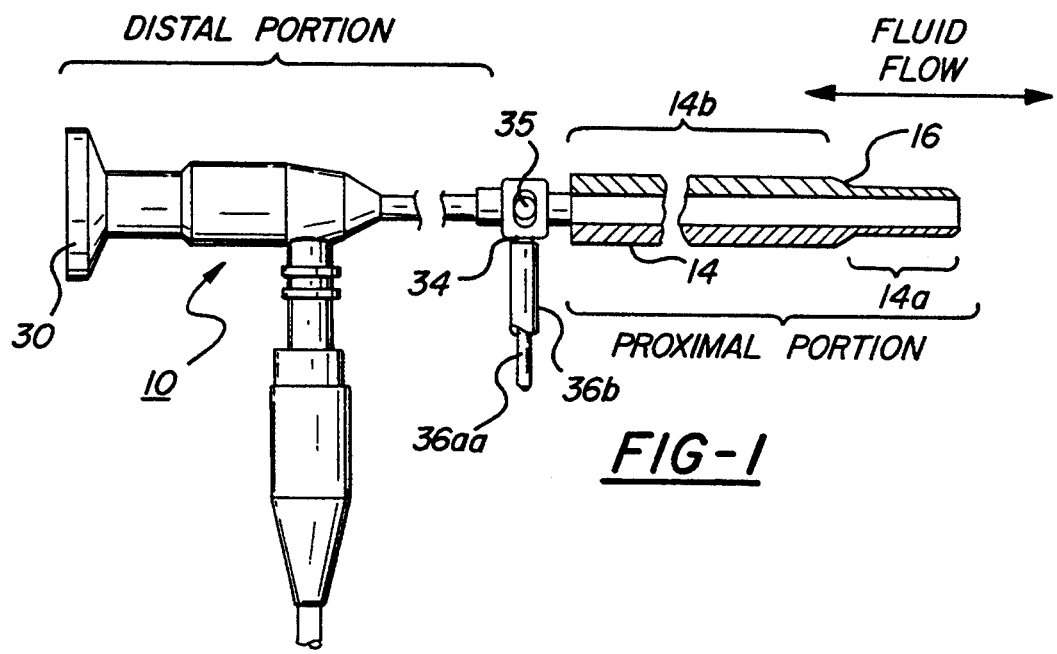
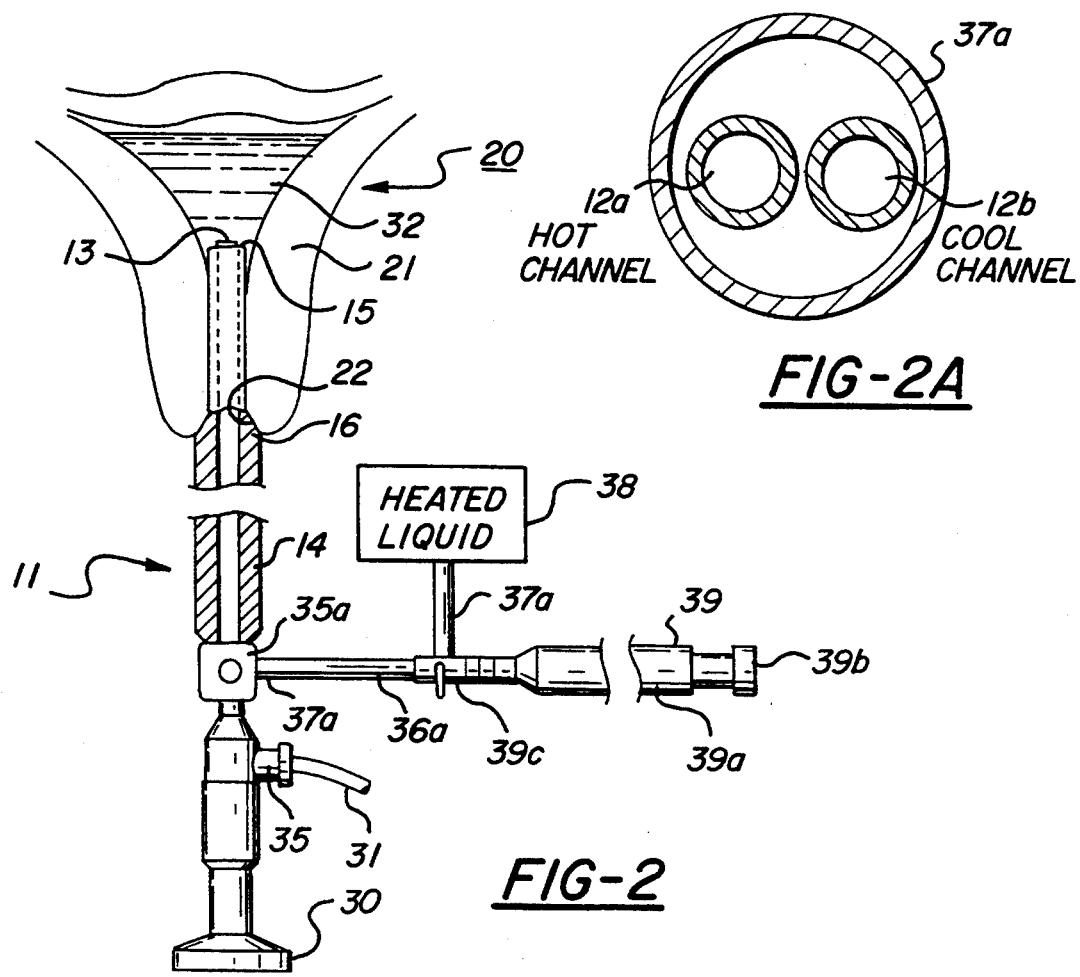

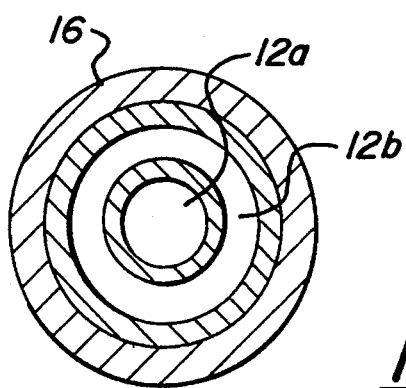
FIG-5
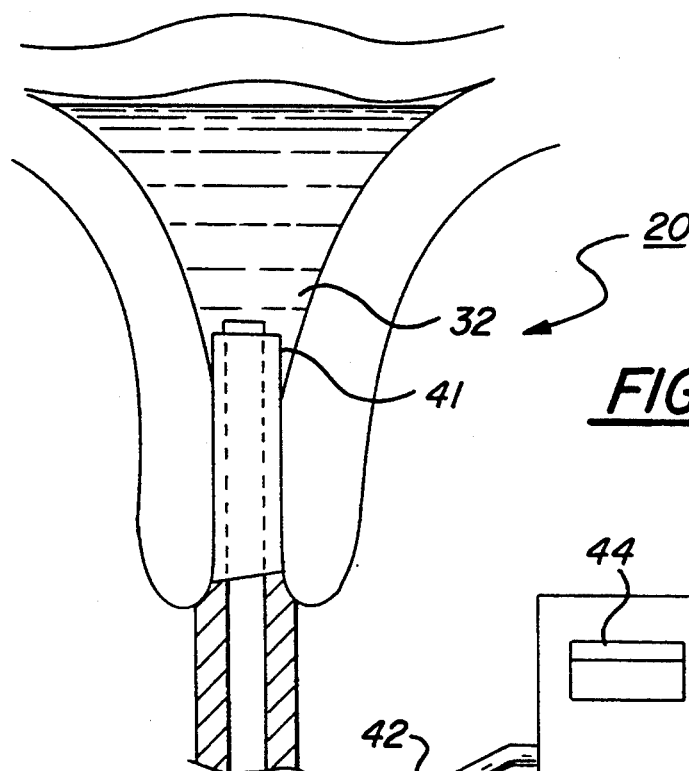
FIG-6
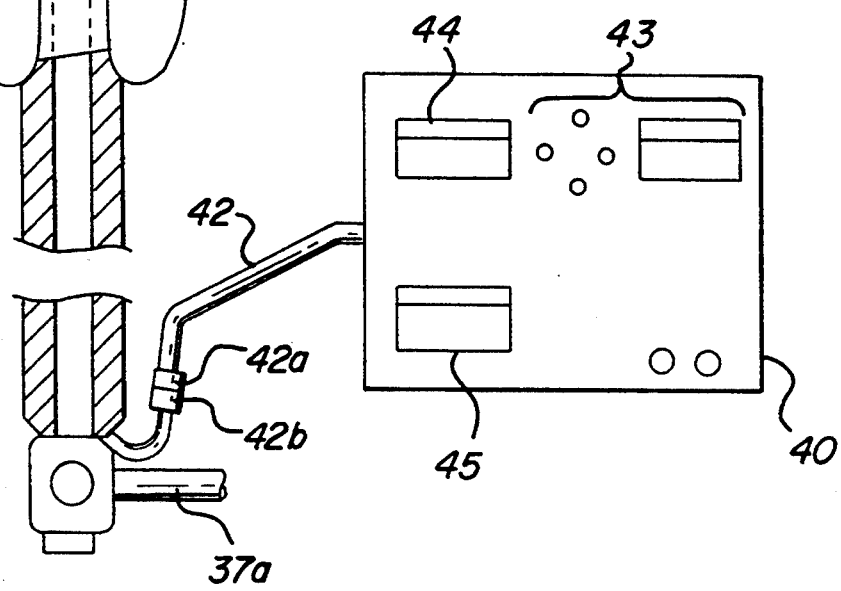

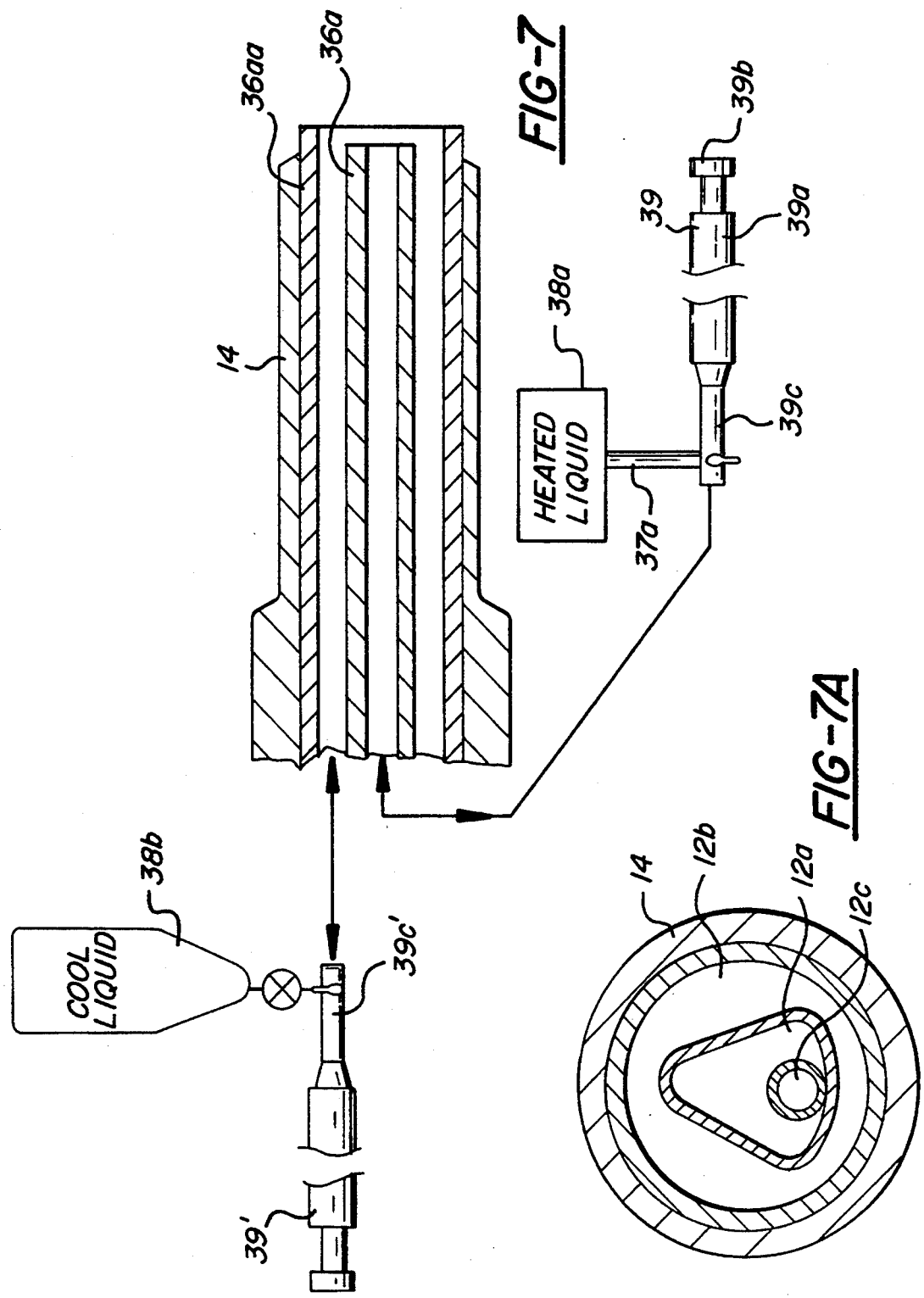

ENDOMETRIUM COAGULATING APPARATUS AND SURGICAL METHOD FOR THERMAL DESTRUCTION OF THE ENDOMETRIUM

This application is a continuation of application Ser. No. 07/695,636, filed May 3, 1991, now U.S. Pat. No. 5,242,390.

FIELD OF THE INVENTION

This invention describes surgical procedures and apparatus for use in thermally destroying the lining of the uterus, known as the endometrium. These procedures are accomplished in a simpler manner than previous techniques utilized for coagulation or cauterization of that portion of the uterus. The endometrium is that portion of the lining that covers the inner surface of the fundus, or top part, of the uterus. This is the portion which bleeds during menstruation and where a developing pregnancy implants. The lower portion of the uterine lining known as the endocervix should be kept intact and should not be destroyed as it contributes to neither menstruation nor fertility.

BACKGROUND OF THE INVENTION

Numerous methods and devices have been described for destruction of the endometrium in order to cause cessation of excessive uterine bleeding or sterilization. Chemical methods have been used and have been uniformly unsuccessful, basically because of the rapid regenerative properties of the tissue to be destroyed. In addition, the chemicals used may be very toxic. Physical methods have fared somewhat better as will be presently described.

In U.S. Pat. No, 3,924,628 Droegemueller et al. describe a method and apparatus for cryogenic destruction of the endometrium utilizing a distending bladder and cryogenic material. This apparatus has had only limited success basically because the procedure is a blind one. Since the blind procedure may produce an incompletely distended or inflated bladder, large areas of the endometrium in such cases are not in adequate contact with the bladder to cause complete destruction of the endometrium. The incomplete destruction of the endometrium allows blood to accumulate within the uterus and produces a painful condition known as hematometra. In addition, perforation of the uterus during blind insertion could cause cryogenic damage to adjacent organs with resultant serious medical complications.

Neuwirth and Bolduc, U.S. Pat. No. 4,949,718, similarly describe a bladder inserted blindly into the uterine cavity with a heating element within the bladder to maintain adequate heat within the unit. The use of the bladder in a blind technique again may not assure contact with the entire endometrial surface. They also describe a 5% dextrose solution used to distend the bladder and an external means to maintain the distending pressure within the bladder. This technique is a blind one and could result in areas of the endometrium being spared, thus yielding results similar to that of Droegemueller et al. In addition, perforation of the uterus by the blind technique could result in thermal injury to adjacent organs.

Other patents that describe thermal methods involving imperfect contact or conformation with the shape of body cavities and also blind approaches are U.S. Pat. Nos. 2,734,508; 2,077,453; 3,369,549; 2,192,768; 2,466,042; and 2,777,445.

The reported successful efforts to effect endometrial destruction have all utilized direct visualization to effect complete destruction of the endometrium. The first successful method was described by Goldrath et al. (M. H. Goldrath, T. A. Fuller, and S. Segal, *Laser Photovaporization of the Endometrium for the Treatment of Menorrhagia*, American Journal of Obstetrics and Gynecology, 104–14, 1981) using the Neodymium:YAG laser under direct vision through a hysteroscope. Intense amounts of thermal energy are applied through a fiber optic to systematically destroy the endometrial surface. This procedure, although admittedly tedious, has been successful. Similar success has been enjoyed by the use of high frequency coagulating current also utilizing direct vision through a hysteroscope. Both of these methods require considerable skill and there is a potential risk of perforation of the uterus which could cause damage to other organs. In addition, since a large amount of fluid is used to distend the uterus for visualization, this fluid may be absorbed into the circulation and if excessive could cause physical problems.

OBJECTS OF THE INVENTION

One object of the present invention is to provide a safe and effective method for thermally destroying the entire endometrial lining of the uterus. Another object is to simplify the procedure whereby it is done under direct vision using a hysteroscope, the heating liquid is injected directly into the uterus through the delivery channel of the hysteroscope, and the liquid is heated externally to the patient, therefore greatly simplifying both the procedure and the instrumentation and assuring application of the heated liquid to all portions of the endometrial lining using only enough pressure necessary to achieve distention of the uterus and dispersion of the heated liquid. A further object is to provide fluoroscopic means for viewing the liquid-distended uterine cavity and the accurate endocervical insertion therein of a hysterographic cannula.

A still further object is to provide thermally insulative probe shield means serving to maximize correct depth of endocervical insertion.

Yet another object is to provide probe shield means incorporating means of thermal measurement in utero.

These and other objects, features and advantages will be realized from the following description.

DETAILED DESCRIPTION OF THE INVENTION

The invention in one preferred embodiment concerns apparatus allowing direct visualization in a surgical procedure for coagulating endometrial tissue of the uterus. The apparatus comprises a hysteroscope having a proximal portion for insertion into the uterus through the vagina and a distal gripping/visualization portion. The hysteroscope comprises both optical means for viewing the uterine cavity and channel means for delivering tissue-coagulating controllably heated liquid into the cavity, as well as thermal insulation means for the hysteroscope which means is sufficiently insulative during the period of the heated liquid transport and the coagulating surgery with the liquid to avoid thermal damage to tissue other than the endometrial tissue (such as vaginal tissue and endocervical tissue). The apparatus also includes liquid supply means for transporting the liquid through the channel means into and from the uterine cavity, and control means for regulating the temperature and pressure of the heated liquid.

The liquid supply means can be a manually operated syringe barrel and plunger containing heated liquid, or other suitable liquid transport means placed in open communication by means of tubing interconnecting with the inlet port of the hysteroscope. The liquid withdrawal means can be a similar means in open communication with the outlet port of the hysteroscope. The control means for regulating the liquid pressure in the uterus can be a manual control achieved by operator pressure on the plunger of the supply syringe. The control means for regulating the liquid temperature can be that of a conventional thermostat-controlled heater in open communication by tubing interconnecting with the syringe barrel. The control means also can be automatic as in the system described by Neuwirth and Bolduc in U.S. Pat. No. 4,979,718, incorporated herewith by reference, especially as to the temperature, pressure and/or time measurement and display functions.

The invention in another preferred embodiment concerns a surgical procedure for completely coagulating endometrial tissue of the uterus comprising the steps of a) distending the uterine cavity with a physiologically compatible aqueous solution (such as saline solution or other suitable liquid) under direct vision by means of a hysteroscope having channel means for delivering and introducing liquid to the uterine cavity under pressure sufficient to inflate and directly expose the entire endometrial surface; b) confirming that the proximal portion of the hysteroscope is properly located within the uterine cavity by appropriate visualization of its internal architecture; c) withdrawing the aqueous solution from the uterine cavity thus causing it to become substantially collapsed; and d) distending the thus collapsed uterine cavity under direct vision by means of said hysteroscope, by delivering and introducing to the uterine cavity aqueous carbohydrate solution (or a suitable equivalent solution) heated to an endometrial tissue-coagulating temperature under pressure sufficient to directly expose the entire endometrial surface and for a time sufficient to keep the heated solution in contact with the entire surface and thereby cause uniform and complete destruction of the endometrium.

Any non-toxic aqueous liquid may be used if it is heat stable. An aqueous dextran clinical solution (Merck Index XI, Abstract 2925) is preferred, more preferably, 32% dextran 70 in 10% glucose in water. The latter solution is known to be clinically safe and effective for hysteroscopy. It may be heated to temperatures well in excess of the boiling point of water and may be kept in continuous contact with the entire endometrium at a temperature (in the range from about 190° to about 230° F.) and for a time sufficient to cause destruction of the endometrium, preferably in the range from about 0.5 to about 5 minutes. When adequate temperature and time have been attained, the fluid can be rapidly cooled preferably by diluting with a physiologic saline solution at ambient temperature or body temperature.

In a preferred embodiment, prior to the step a) or step d) of distending the uterine cavity, the present procedure in a patient who has not had a prior tubal sterilization optionally includes the step of blocking the oviducts such as by applying silicone polymer (Silastic TM) rings laparoscopically to the Fallopian tubes so as to thereafter prevent in step d) spill of the heated liquid which may otherwise occur through the Fallopian tubes to adjacent tissue. Alternatively, in a preferred embodiment, the procedure includes for preventing such damage from leakage of the heated liquid, optionally filling the lower abdomen cavity with a suitable volume, e.g. one liter, of physiologic saline introduced by injection through the cul de sac.

The invention in another preferred embodiment concerns a surgical procedure for completely coagulating endometrial tissue of the uterus comprising the steps of (a) distending the uterine cavity with a fluoroscopically radio-opaque physiologically compatible solution under indirect vision by means of a hysterographic cannula having a proximal portion including probe means and insulative probe sheath means limiting the depth of endocervical insertion and further having channel means for delivery and introducing liquid to the uterine cavity under pressure sufficient to inflate and directly expose the entire endometrial surface; (b) confirming that the proximal portion of the hysterographic cannula is properly located within the uterine cavity and that the cavity is properly inflated by fluoroscopic visualization of the internal architecture of the cavity relative to said proximal portion; (c) withdrawing said solution from the uterine cavity thus causing the cavity to become substantially collapsed; and (d) distending the thus collapsed uterine cavity under fluoroscopic vision by means of said hysterographic cannula, by delivering and introducing to the uterine cavity an aqueous radiopaque solution heated to an endometrial tissue-coagulating temperature under pressure sufficient to fluoroscopically expose the entire endometrial surface and for a time sufficient to keep the heated solution in contact with said entire surface and thereby cause time/temperature dependent destruction of the endometrium. For this procedure one may use any suitable radiopaque heat stabile solution such as Hypaque Sodium (Merck Index XI, Abstract 2975) or similar pharmaceutically acceptable solution mixed with the dextran solution in sufficient quantity for fluoroscopic visualization.

BRIEF DESCRIPTION OF THE DRAWINGS

FIG. 1 depicts a hysteroscope in a preferred embodiment with accompanying insulated sheath means in the proximal portion for handling heated liquid in order to thermally insulate and thereby prevent unwanted thermal damage to tissues other than endometrium from contact with the hot instrument; also in the proximal portion to enable the practitioner to be comfortable in the manipulation of that portion of the hysteroscope;

FIG. 2 depicts the use of a hysteroscope apparatus for endocervical insertion in a preferred embodiment including a vessel for holding heated liquid and a delivery system with temperature and pressure control means including a heat resistant plastic syringe and insulated tubing to deliver the heated solution into the syringe and then into the hysteroscope. The insulated tubing is necessary to give adequate protection to the operator. Uterine distension may be maintained by pressure on the plunger of the syringe;

FIG. 2A is a cross-sectional view of an insulative liquid supply/withdrawal tube;

FIG. 5 is a cross-section of FIG. 4 taken on line 5—5;

FIG. 6 is a view showing in a preferred embodiment the location of thermocouple sensor means for a hysteroscope probe shield or insulated hysterographic cannula connected by electrical leads via attachable and detachable female and male electrical connectors to a temperature display unit.

FIG. 7 is a schematic view of a preferred embodiment of a system for the delivery and withdrawal of fluids through a hysteroscope; and FIG. 7A is a cross-sectional view in a preferred embodiment of the probe 11 of an insulative hysteroscope according to the invention.

DETAILED DESCRIPTION OF THE PREFERRED EMBODIMENT

Figure 4:
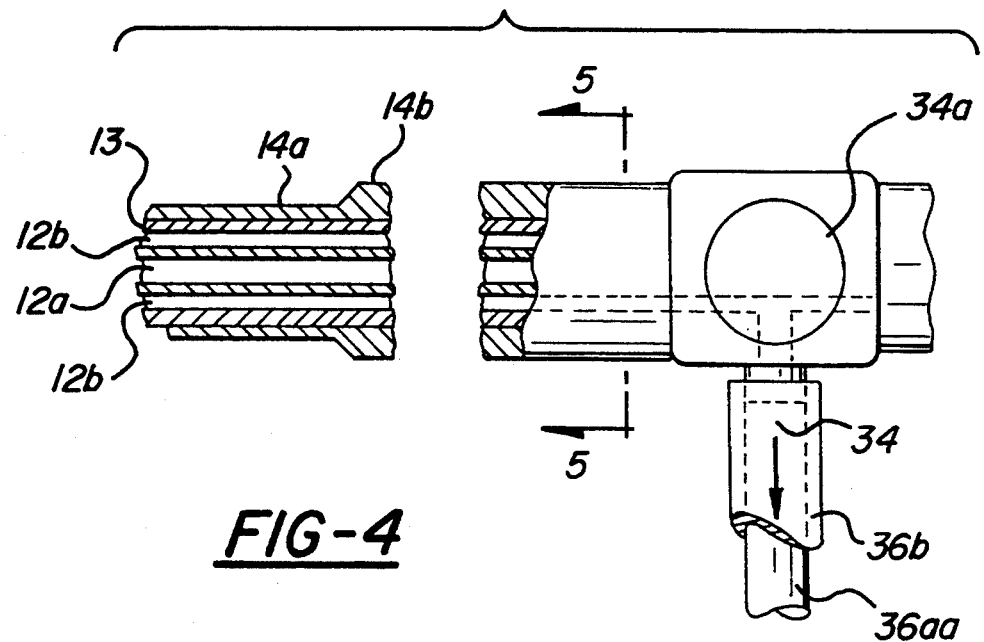
FIG. 4 is a view partly in section illustrating channel means for liquid supply and removal of liquid.

The invention in a preferred embodiment comprises a hysteroscope 10 (shown in FIG. 1) having a proximal portion and a distal portion. The proximal portion includes a delivery probe or barrel 11 of suitable length for endocervical insertion into the uterus and having concentric open channels 12a and 12b (shown in FIGS. 4 and 5) for fluid transfer via the probe tip 13 to and from the uterine cavity. The telescope 12c includes fiber optic cables (not shown) for illumination and viewing through viewing and illumination windows located at the tip end. The probe 11 is thermally shielded on its exterior surface by a substantially co-extensive telescopically fitting rigid or semi-rigid heat-insulative concentric tubular sheath 14. The sheath as shown has a annular shoulder 16 contoured for contact with the exterior surface 23 of the cervix that serves to limit further intrauterine insertion of the hysteroscope. The sheath can be made of any suitable insulative porous or non-porous material such as fiberglass, rubber, styrofoam, and the like, e.g., about one and one-half mm. in the portion 14a inserted and about seven mm. thick in the portion 14b including the shoulder. In one preferred embodiment the probe or barrel 11 which is usually made of metal may instead be made of insulative rigid or semi-rigid non-metallic polymeric material having the geometry of the barrel and the protective sheath so that the sheath need not be separate from the barrel, and preferably can be attached and detached from the hysteroscope (as a disposable item) e.g., by threadable means at its distal end. The distal portion includes the hollow barrel 11, an eye piece 30, associated viewing and illumination light. guide cables (not shown), and a supply light guide cable 31. Located between the proximal and distal portions is a fluid port 35 communicating via a valve 35a with the open inlet channel 12a of the barrel. The fluid port is open communication with a flexible fluid transfer tube 36a (shown in FIG. 2) that is thermally insulated by a flexible exterior concentric tubular sheath 37a. In another embodiment, an insulative fluid transfer tube having dual channels 12a,12b hot and cool (e.g., color coded red and green) respectively, which dual transfer tube is employed in a thermally insulative sheath 37a with the preferred system shown in FIG. 7. The latter system is operated under the positive and negative pressure control from two syringes 39,39' by 3-way valves 39c,39c'. Thus, for example, once the system is filled with cool or ambient physiologic saline fluid free of bubbles, the valves are set for intrauterine delivery of the fluid via the probe 11, with bubble-free replenishment of fluid from the supply reservoir 38b. When the ambient fluid is to be replaced in the uterus by heated fluid, the valves are reset so that the cool reservoir 38b is out of circuit and the heated reservoir 38a is in circuit. The hot liquid-delivery syringe 39 is then aspirated to fill it with hot liquid and thus (with reservoir 38a again out of circuit) is delivered to the uterus while the other syringe 39' is aspirated to remove the ambient fluid for disposal via exit port 34 to a reservoir (not shown). In turn, when the intrauterine coagulation exposure has been achieved, the procedure is reversed so that negative aspirating pressure of syringe 39 removes the heated liquid from the uterus via port 35 for disposal to a reservoir (not shown) while the heated liquid is being replaced in the uterus with cool saline resupplied via syringe 39'.

For endocervical insertion of a hysteroscope (shown in FIG. 2) according to the invention the proximal portion of the hysteroscope is surgically inserted within a human uterus 20 inflated with a liquid 32 under pressure serving to distend the uterine cavity and to thereby insure that the entire surface of the endometrial tissue layer 21 is exposed for direct vision by means of the hysteroscope, thus enabling direct observation of the uterine cavity architecture. Care is taken throughout the procedure to avoid the formation of air bubbles in the system 12 especially in utero since such air entrainment would diminish the desired heated liquid contact with the layer 21 during the coagulation step. Also shown, as described, is the correct placement of the insulative sheath 14 and sheath shoulder 16 so that when the shoulder fully abuts against the cervical surface thereby preventing further insertion, the probe tip 13 is ideally located within the uterine cavity.

Figure 3:
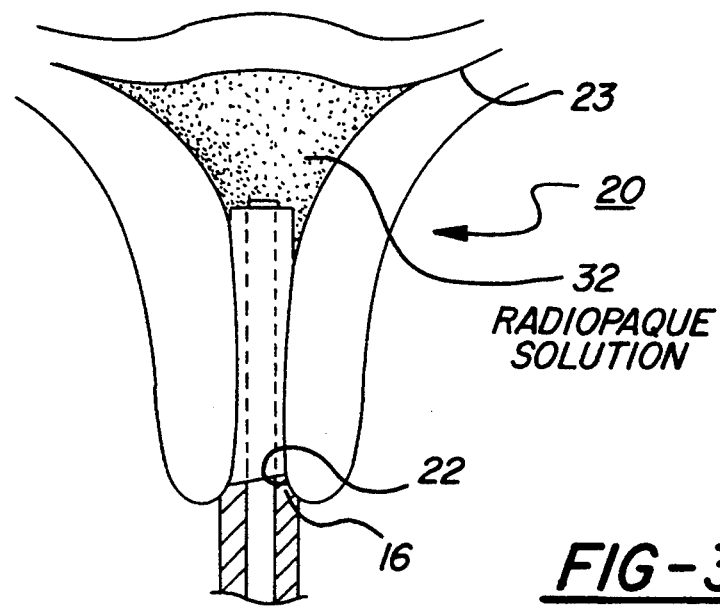
FIG. 3 depicts a view of the distended uterine cavity containing radiopaque liquid and of the insulated hysterographic cannula inserted into the cavity under fluoroscopic control confirming that the intracervical insertion and the uterine distension are both correct. This provides an indirect visualization of the uterine cavity to provide great assurance that the fluid is delivered into and only into the endometrial cavity and not into external organs.

Alternatively, correct intrauterine placement of the hysterographic cannula tip can be confirmed by filling the uterine cavity with a fluoroscopically opaque solution (shown in FIG. 3) such as dextran solution containing Hypaque sodium (Merck Index XI, Abstract 2975) or other suitable radiopaque solution and viewing the cavity fluoroscopically. Also alternatively, correct intrauterine placement of the hysterographic cannula tip can be confirmed by ultrasonic viewing.

The hysterographic cannula and the hysteroscopic probe both include a fluid outlet port 34 communicating through a valve 34b with the return channel 12b for disposal through a flexible fluid transfer tube 36aa that is thermally insulated by a flexible tubular sheath 36b. The fluid inlet port 35 in turn (FIG. 1) is in open communication via the fluid transfer tube 36a (FIG. 2) with liquid/fluid transfer means which includes a heated liquid reservoir 38a and a syringe 39 with a barrel 39a and a plunger 39b. The barrel and the reservoir can be placed in open communication through the fluid transfer tube by way of a syringe 3-way valve 39c. The sensor means for monitoring the liquid temperature comprises a thermocouple 41 (shown in FIG. 6) in the probe sheath exterior connected by electrical leads (not shown) from the control unit 49 (comprising a fluid temperature display 43, fluid pressure display 44, and time control and display 45), protected by an electrical sheath 42. Female and male electrical lead connectors 42a,42b enable the attachment and detachment of the sheath 14 from the display unit 40.

EXAMPLE

The thermal destruction of the endometrium (endometrial ablation) according to the present invention is suitable for patients of the type previously described by Goldrath et al (M. H. Goldrath, T. A. Fuller, and S. Segal, *Laser Photovaporization of the Endometrium for the Treatment of Menorrhagia*, American Journal of Obstetrics and Gynecology, 104-14, 1981). The procedure results in sterility and indeed could be considered to be a sterilization procedure. In the present procedure, adequate preoperative evaluation includes as a preliminary step ruling out endometrial and cervical cancer and its precursors. The procedure may be performed in the presence of fibroids and with a direct application of the heated liquid in utero. Moderate sized fibroids and moderately large uterine cavities are not a contraindication to the procedure. Preoperative medication with suitable modalities to induce endometrial atrophy may prove to be efficacious but may not be necessary. If these preoperative medications are not used, the procedure should be performed immediately postmenstrually. The procedure may be performed under local or general anesthesia.

In patients who have not had a prior tubal sterilization, the application of silicone polymer (Silastic TM) rings, laparoscopically to the Fallopian tubes serves to prevent spill of the hot liquid which may otherwise occur through the Fallopian tubes. Alternatively, such damage from the hot liquid is prevented by filling the lower abdominal cavity with one liter of physiologic saline introduced by injection through the cul de sac. This preferably is removed following the procedure. Any small amount of hot liquid which escapes through the Fallopian tubes is rapidly cooled in situ by the large amount of post-op added saline solution.

The cervix is grasped with a tenaculum and a paracervical block of Marcaine ¼% with epinephrine 1:200,000 is given. This serves to relieve pain during the procedure and relieve post-operative pain. The cervix is dilated sufficiently to admit the hysteroscope with the insulative sheath through the cervix into the uterine cavity ensuring a tight fit. Visualization is accomplished by distending the uterine cavity with a physiologic saline solution. If there is any evidence of perforation one should not proceed with the procedure. Assuming satisfactory visualization, the previously heated liquid, preferably 32% dextran 70 in 10% glucose in water, is brought into the large syringe 39 through the insulated tubing and the stopcock is then closed. The saline solution is withdrawn (e.g., by aspiration with a syringe via exit port 34) from the endometrial cavity causing it to collapse and then the hot liquid is delivered into the uterine cavity under direct vision with enough pressure to cause visual distention of the cavity. The distention is maintained for a sufficient time as correlated with the delivery temperature. After a sufficient time has elapsed, the system is flooded with physiologic saline which rapidly cools the instrumentation and the carbohydrate solution which is within the uterus. The solution is then withdrawn and the instrumentation is removed. The procedure is then complete. An optional procedure is to use a fluoroscopically radiopaque heated solution, as described, instead of the heated liquid just mentioned for purposes of coagulation under the same time/temperature conditions and under indirect vision.

What is desired to claim as my exclusive property in the invention, as described, is the following:

1. Apparatus allowing direct visualization of a cervix, a uterus and its uterine cavity with an endometrial surface in a surgical procedures for coagulating the endometrial surface of the uterus comprising:
    a hysteroscope having a proximal portion for endocervical insertion at a depth into the uterus and a distal portion, and including a hollow barrel having optical means for viewing the uterine cavity disposed therein and, in the proximal portion, forming a hollow probe having an exterior surface and channel means for delivering tissue-coagulating heated liquid for a period of time at a selected temperature in direct contact with endometrium tissue lining the uterine cavity;
    thermally insulative sheath means disposed concentrically around said probe, which means is sufficiently insulative to avoid thermal damage to tissue other than said endometrial tissue during the period of said delivery;
    liquid transfer means in fluid communication with said channel for delivering heated liquid through said probe to and from the uterine cavity; and
    control means operatively associated with the probe for regulating the temperature of said liquid.

2. The apparatus of claim 1 wherein said thermally insulative sheath means further includes a shoulder means of increased lateral dimension contoured for contact with the exterior surface of the cervix.

3. Apparatus according to claim 1 where the probe is tubular in shape and the thermally insulative means comprises a tubular sheath telescopically engaging and covering the exterior surface of the probe.

4. Apparatus according to claim 3 where the tubular sheath comprises a tip end including thermocouple sensor means for determining the intrauterine temperature.

5. Apparatus according to claim 1 where the liquid transfer means comprises thermally insulated tubing in open communication with said hollow probe and channel means.

6. Apparatus according to claim 5 where the liquid transfer means comprises syringe means in open communication with said insulative tubing.

7. A surgical procedure for coagulating endometrial tissue of the uterus comprising distending the uterine cavity by filling the cavity and directly contacting the endometrial surface with a heated physiologically compatible solution under pressure sufficient to inflate and directly expose substantially the entire endometrial surface for a time sufficient to cause time and temperature dependent destruction of the endometrium.

8. A surgical procedure for coagulating endometrial tissue of a uterus adjacent to oviducts, Fallopian tubes, and a lower abdominal cavity, said uterus having a uterine cavity with an endometrial surface and an internal architecture, and further having a cervix with an exterior surface, comprising the steps of:
    a) distending the uterine cavity with a physiologically compatible solution under direct vision by means of a hysteroscope having a proximal portion for endocervical insertion at a depth into the uterus, said proximal portion including probe means and insulative probe sheath means and further having channel means for delivering and introducing liquid to the uterine cavity under pressure sufficient to inflate and directly expose the endometrial surface;

b) confirming that the proximal portion of the hysteroscope is properly located within the uterine cavity and that the cavity is properly inflated by visualization of the internal architecture of the cavity relative to said proximal portion;

c) withdrawing said solution from the uterine cavity, thus causing the cavity to become substantially collapsed; and d) distending the uterine cavity while said cavity is under direct vision by means of said hysteroscope, by delivering and introducing to the uterine cavity an aqueous solution that is heated to an endometrial tissue-coagulating temperature and under pressure sufficient to directly contact and expose the endometrial surface for a time sufficient to thereby cause the destruction thereof.

9. A surgical procedure for coagulating endometrial tissue of a uterus having, adjacent to oviducts, Fallopian tubes, and a lower abdominal cavity, a uterine cavity with an endometrial surface and an internal architecture, comprising the steps of:

a) distending the uterine cavity with a fluoroscopically radiopaque, physiologically compatible solution under indirect vision by means of a hysteroscopic cannula for endocervical insertion at a depth into the uterus, said cannula having a proximal portion including probe means and insulative probe sheath means and further having channel means for delivery and introducing liquid to the uterine cavity under pressure sufficient to inflate the endometrial surface;

b) confirming that the proximal portion of the hysteroscope is properly located within the uterine cavity and that the cavity is properly inflated by fluoroscopic visualization of the internal architecture of the cavity relative to said proximal portion;

c) withdrawing said solution from the uterine cavity, thus causing the cavity to become substantially collapsed; and d) distending the uterine cavity while said cavity is under indirect fluoroscopic vision by means of said hysteroscopic cannula, by delivering and introducing to the uterine cavity aqueous, radiopaque solution heated to an endometrial tissue-coagulating temperature and under pressure sufficient to directly expose the endometrial surface, and keeping the heated solution in contact with said surface for a time sufficient to thereby cause the destruction thereof.

* * * * *